(12) United States Patent
Duff

(10) Patent No.: US 8,673,885 B1
(45) Date of Patent: Mar. 18, 2014

(54) COMPOUNDS FOR THE PROTECTION OF SULFUR CONTAINING LINKERS IN NUCLEIC ACID SYNTHESIS

(76) Inventor: Robert Duff, York, PA (US)

( * ) Notice: Subject to any disclaimer, the term of this patent is extended or adjusted under 35 U.S.C. 154(b) by 226 days.

(21) Appl. No.: 13/189,601

(22) Filed: Jul. 25, 2011

Related U.S. Application Data

(60) Provisional application No. 61/367,435, filed on Jul. 25, 2010.

(51) Int. Cl.
*C07F 9/6512* (2006.01)
*C07F 9/22* (2006.01)
*A61K 31/664* (2006.01)

(52) U.S. Cl.
USPC .................. 514/86; 514/112; 544/243; 558/2

(58) Field of Classification Search
USPC ........................... 558/2; 514/112, 86; 544/243
See application file for complete search history.

(56) References Cited

U.S. PATENT DOCUMENTS 3,755,506 A * 8/1973 Gutman ............................ 558/2
2009/0082554 A1 3/2009 Dellinger et al.

OTHER PUBLICATIONS

Berger et al., Poly-L-cysteine, J Am Chem Soc 78:4483-4488, 1956.
Brownlee et al., Amino-acids . . . of peptides, J Chem Soc 3832-3840, 1964.
Nokihara et al., Studies on . . . For cysteine, J Org Chem 43:4893-4895, 1978.
Zervas et al., On cysteine . . . peptide synthesis, J Am Chem Soc 85:1337-1341, 1963.
West et al., New methods . . . protection of cysteine, Org Lett 3:1205-1208, 2001.
Sokolovsky et al., Nonenzymatic cleavage . . . cysteinyl peptides, J Am Chem Soc 86:1213-1217, 1964.
Hiskey et al., Sulfur-containing . . . protective group, J Org Chem 35:215-220, 1970.
de la Torre et al., Use of a . . . at the 5'-end, Nucleosides & Nucleotides, 12:993-1005, 1993.

\* cited by examiner

*Primary Examiner* — Deepak Rao
(74) *Attorney, Agent, or Firm* — MDIP LLC

(57) ABSTRACT

Aromatic and alkyl thiocarbonates with and without a neighboring group that participates in the hydrolysis of a thiocarbonate are described. The aromatic or alkyl thiocarbonates can be used for the protection of sulfur during oligonucleotide synthesis. Their facile processes of manufacture and methods of using the same are provided.

4 Claims, No Drawings

COMPOUNDS FOR THE PROTECTION OF SULFUR CONTAINING LINKERS IN NUCLEIC ACID SYNTHESIS

This application is a non-provisional application claiming benefit to the 25 Jul. 2010 filing date of U.S. Ser. No. 61/367,435, the entire contents of which are incorporated herein by reference in entirety.

FIELD OF THE INVENTION

This invention pertains to compounds that protect a sulfur, for example, during oligonucleotide synthesis. In one embodiment, the invention relates to a thiocarbonate moiety. In another embodiment, the invention relates to an aryloxycarbonyl or alkyloxycarbonyl thiocarbonate. The thiocarbonate can be removed by intermolecular or intramolecular nucleophiles.

BACKGROUND OF THE INVENTION

Benzyloxycarbonyl compounds are known in the literature as protecting groups for amines and in some examples as a protecting group for hydroxyl moieties. This group of compounds has been used in solid phase peptide synthesis (SPPS) because of the ease in which the group is removed through hydrogenation or hydrobromic acid treatment. Similarly, thiocarbonates are known and have been reviewed. Various chemical protection and deprotection strategies have been provided by Berger et al. (*J. Am. Chem. Soc.* 1956, 78, 4483), Zervas et al. (*J. Am. Chem. Soc.* 1963, 85, 1337), Sokolovsky et al. (*J. Am. Chem. Soc.* 1964, 78, 1202).

A previous study explored the use of an S-isobutyloxymethyl protective group. Young et al. (Young, G. T.; Brownlee, P. J. E.; Cox, M. E.; Handford, B. O.; Marsden, J. C. *J. Chem. Soc.* 1964, 3832) discovered that this group was stable to 2 N hydrochloric acid and 50% acetic acid, and decomposed slightly in 2 N sodium hydroxide. Hiskey et al. (Hiskey, R. G.; Sparrow, J. T. *J. Org. Chem.* 1970, 35, 215-220) teaches that cysteines in SPPS may be protected during chain elongation with the S-isobutyloxymethyl protective group. This group was stable in 12 N hydrochloric acid in acetone, warm aqueous acetic acid and hydrazine hydrate in refluxing ethanol. It showed decomposition to silver nitrate in ethanol and boron trifluoride etherate in acetic acid.

None of these references was applied to oligonucleotide synthesis nor did the references address the sensitivities of the deprotection strategies. In fact, the current invention demonstrated that the S-benzyloxycarbonyl (S-CBz) thiol-modified six-carbon linker was stable to concentrated ammonia (30% v/v) for ~18 h, but was completely hydrolyzed by dilute sodium hydroxide in short periods. This was an unexpected result.

Dellinger et al (U.S. Ser. No. 11/903,821; US 2009/0082554) teaches the use of thiocarbonate linkers for polynucleotides. These inventors employ the thiocarbonate moiety as cleavable linkers between an oligonucleotide and protein, ligand (consists of a drug carrier, drug, targeting molecule, or molecules that can improve intercellular or intracellular transport) or a solid support used for oligonucleotide synthesis such as TENTA gel. It is not clear from their teachings that this thiocarbonate linkage could be used to protect a sulfur atom when applying a thiol modifier at the 5'-terminus of the oligonucleotide and upon nucleophilic release post-oligonucleotide synthesis enables the 5'-thiol-modified oligonucleotide to participate in a Michael reaction with a Michael acceptor molecule.

Nokihara et al. (Nokihara, K.; Berndt, H. *J. Org. Chem.* 1978, 43, 4893-4895) teaches that the carbobenzoxy (CBz) group may be used to protect disulfide forms (sulfenyl) of cysteine in peptide synthesis. It is stable to trifluoroacetic acid treatment and mild alkali conditions. It is unstable to strong alkali treatment. It is not clear from their teachings that this group could be used for oligonucleotide synthesis and its deprotection scheme.

Currently, several reagents are available for the addition of thiol groups on an oligonucleotide. One is S-Bz TEG-CE phosphoramidite (Link Technologies, Item Number: 2187, United Kingdom). This phosphoramidite synthon is protected by the benzoyl (Bz) group.

This current invention comprises the S-benzyloxycarbonyl (S-CBz) group instead of the thiobenzoyl (S-Bz) group. Studies have shown that that the S-Bz group is too labile to hydrolysis and would not remain attached to the oligonucleotide during deprotection of the phosphate groups and bases. Because there is no selective deprotection, the fully deprotected oligonucleotide with thiol could undergo dimerization (disulfide formation) at the appropriate pH.

The 5'-thiol modifier, C6 (S-trityl-6-mercaptohexyl-(2-cyanoethyl)-N,N'-diisopropyl-phosphoramidite (Glen Research, item number 10-1926-xx) uses the standard phosphoramidite chemistry for insertion and is stable to premature removal due to the robustness of the triphenylmethyl (trityl)-derivatized thioether bond. To deprotect the thiol group, a heavy metal is required. Silver nitrate solution (1 M) is used at room temperature for 30 minutes.

This current invention does not require a heavy metal for deprotection. As a result, there would be no need to remove the metal from the reaction solution, thereby facilitating the final purification.

The 5'-thiol modifier, C6 S—S (1-O-dimethoxytrityl-hexyl-disulfide, 1'-[(2-cyanoethyl)-(N,N'-diisopropyl)]-phosphoramidite (Glen Research, item number 10-1936-xx) uses the standard phosphoramidite chemistry for insertion and is stable to premature removal due to the robustness of the disulfide bond (as indicated by the S—S term in the name). To deprotect the thiol group, a reducing agent is required, such a β-mercaptoethanol, dithiothreitol (DTT) or tris(carboxyethyl)phosphine (TCEP). Typically, a concentrated DTT solution (~0.5 M) is used at room temperature or slightly elevated temperature for 30 minutes. The by-product of this reduction is a mole equivalent of the protecting thiol counterpart which must be removed or sequestered prior to use for subsequent conjugation reactions (e.g. Michael reaction).

This current invention does not yield such reactive by-products in the deprotection reaction or process. As a result, there would be facilitation of the final purification.

Reactive by-products are also produced in β-elimination reactions where the sulfur is protected by a thioether. As a result of basic or acidic treatment, the by-product could be an alkene. If not carefully removed, this unsaturated product may react with the thiol. An example of this would be the following study.

West et al. (West, C. W.; Estiarte, M. A.; Rich, D. H. *Org. Lett.* 2001, 3(8), 1205-1208) teaches that the 9-fluorenylmethyloxycarbonyl (FMOC) group may be used in the protection of the cysteine side chain in solid phase peptide synthesis (SPPS. They link an aromatic moiety to the sulfur through a thiocarbonate group. As the investigators point out, this strategy has a drawback that re-deployment of the aromatic fluorine moiety can ensue to form an alkylated species linked through a thioether bond. The introduction of a fluorine group into the synthesis route with oligonucleotides can cause immediate termination of the synthesis as this group is removed under conditions too harsh to maintain the integrity of the oligomer.

In addition, De La Torre et al. (de la Torre, B. G.; Avino, A. M.; Escarceller, M.; Royo, M.; Albericio, F.; Eritja, R. *Nucleosides & Nucleotides* 1993, 12(9), 993-1005) teach that the base-labile group, dinitrophenylethyl (DNPE) can be successfully employed for the purpose of oligonucleotide synthesis. A series of oligonucleotides were synthesized and modified with a linker containing this functionality. The by-product of this reaction is dinitrophenylethylene, which may re-react with the thiol if not removed or sequestered.

This present invention was designed to avoid this recombination, as the by-product of the deprotection reaction is a benzyl alcohol. Moreover, due to the lack of β hydrogens with the benzyl group, there is no possibility of reactive unsaturated compounds forming.

Common methodologies to install a sulfur-containing group into an oligonucleotide sequence entails the use of either a triphenylmethyl (trityl group, linked through an acid-labile thioether or a 4,4'-dimethoxytriphenyl C6 alkyl group, linked through disulfide. Functionally, the steric bulk of the trityl group protects the sulfur, while the lipophilicity of the three phenyl moieties aids in the purification by reverse phase methods. The disulfide synthon has wide scale applicability for use as a 3'-modifier, 5'-modifier or internal modifier. The installation of these agents is accomplished through the standard phosphoramidite chemistry.

However, to remove the trityl group, deprotection methods require the presence of heavy metals. Moreover under these conditions, there is a greater risk of oligonucleotide depurination. To ease the conditions necessary for deprotection, monomethoxytrityl (MMT) and dimethoxytrityl (DMT) groups have been explored. While the DMT on oxygen is well established as the optimized 5'-hydroxyl moiety, its utility as a thiol-protecting group is limited by the nature of the sulfur atom resulting in greater sensitivity to DNA synthesis conditions.

The disulfide group is homolytically cleaved by reducing agents such as dithiothreitol (DTT) or tris(carboxy)ethyl phosphine (TCEP) to liberate the thiol. The by-product of homolytic cleavage would be another thiol, which, if not removed by chromatography or other means, could react with target molecule and could reduce the overall yield by 50%. Therefore, a new protecting group was sought, as these strategies were considered inappropriate.

Despite the utility of these protecting groups, the literature is deficient in base labile protecting groups for sulfur. Clearly, these protecting groups are not applicable or suitable for all cases. Specifically, this invention describes the use of the CBz group and outlines the use of modified CBz groups for the protection of a thiol functionality in oligonucleotide synthesis. Additional aromatic and alkyl thiocarbonates are included. Examples are provided to support the use of the CBz-protecting group as a 5'-modifier in oligonucleotides.

SUMMARY OF THE INVENTION

An object of this invention is to provide materials and methods for modifying the 5'-terminus of an oligonucleotide with a linker bearing a thiol group protected as a thiocarbonate group, which is selectively cleaved post removal of other protecting groups (i.e. phosphodiester protection and base protecting groups).

A second object is to provide a method for synthesis of a S-CBz thiol-modified nucleic acid and effective removal of the S-CBz protecting group.

A third object is the use of alternately substituted aromatic thiocarbonate moieties, such as, larger aromatic moieties, such as, naphthalene, anthracene, quinoline, acridine, phenazine, or bicyclic structures, such as, pyrrole-substituted or imidazole-substituted phenyl groups (such as, at the ortho position to give biphenyls) or equivalent ring sizes to phenyl, such as, pyridine, pyrazine, and pyrimidine. The larger aromatic rings provide electron density to the intervening methylene group thereby stabilizing the thiocarbonate against nucleophilic attack. Conversely, the electron deficient aromatic rings, such as pyrimidine, would pull electron density away from the methylene group, thereby increasing the susceptibility of hydrolysis (Example 4).

A fourth object is to provide an orthogonal protection strategy by synthesizing one of the protecting group-bearing synthons (Examples 5 and 6).

A fifth object is to provide a method for synthesizing an S-CBz-protected thiol or modified S-CBz-modified oligonucleotide (Example 9) and removal of the S-CBz or a modified S-CBz protecting group post-deprotection of other moieties (Example 10).

A sixth object is to provide a method for the synthesis of an S-CBz-protected thiol or modified S-CBz thiol modifier (Example 10).

Those and other objects were obtained in the development of a thiocarbonate to form S-protecting CBz and related congeners, which can be applied to oligonucleotide synthesis. The S-CBz protecting groups are cleaved under nucleophilic or basic conditions (intermolecularly or intramolecularly).

Advantageously, the thiol group is released selectively by basic conditions, and a thiol oligonucleotide is then ready for conjugation. Selectivity of deprotection is a crucial advantage as the S-CBz (thiol protecting group) must be last to be removed prior to subsequent reactions, such as conjugation.

An additional advantage of this invention is the independence of using reducing agents (required for disulfide-based protecting groups). Thus, purification is facilitated and the risk of non-product forming side reactions is negated. The presence of the side product, a second thiol group (i.e. 6-mercaptohexanol) would require purification prior to conjugation.

Similarly, there is no need for heavy metals to induce the removal of the protecting group, as commonly performed in thioether protection schemes. In addition, the use of the CBz protecting group avoids rearrangements as commonly found in S-FMOC protections. West et al. (supra) demonstrated that the S-FMOC group would undergo a re-arrangement to give the fluorenylthioether (FM) moiety.

A general formula of a compound of the invention is:

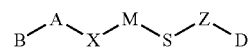

wherein B is an aryl, heteroaryl or alkyl (branched or linear from 1 to about 20 carbons in size) moiety of electron donating or withdrawing characteristics; A is a methylene; X is a heteroatom, such as O, S, or N; M is carbonyl, thiocarbonyl, or imine, and can be a part of a carboxylic, thiocarboxylic, amide, imidate, amidate, thioimidate, thioamidate, ester or thioester group; S is sulfur; Z is an aliphatic hydrocarbon from 1 to about 20 carbons in size, and D is an activated phosphoryl group (which is a group that is capable of forming a phosphate group after a chemical transformation reaction, which includes phosphoryl halogens and phosphoramidites.)

The term "aryl" as used herein refers to an aromatic species containing 1 to 5 aromatic rings, either fused or linked and either unsubstituted or substituted. One or more rings can carry one or more substituents, which may be the same or different in a ring.

The term "heteroaryl" refers to a 5-membered or 6-membered monocyclic structure or to an eight-membered to eleven-membered bicyclic structure which is either saturated or unsaturated. More than one heteroatom can be contained in a ring, and the heteroatoms can be the same or different. Rings can carry different heteroatoms. Examples of heteroatoms include O, S and N.

The term "alkyl" as used herein, unless otherwise specified, refers to a saturated straight chain, branched or cyclic hydrocarbon group of 1 to 20 carbons, such as, but not limited to methyl, ethyl, propyl, cyclopentyl, and cyclohexyl.

The term "alkenyl" as used herein, unless otherwise specified, refers to a branched, unbranched, or cyclic (e.g. in the case of C5 and C6) hydrocarbon group of 2 to 20 carbon atoms containing at least one carbon-carbon double bond, such as, but not limited to ethenyl, vinyl, and allyl.

The term "aliphatic" refers to a cyclic or linear hydrocarbon, which can be branched, can contain one or more unsaturated bonds, and which can carry substituents.

The term "activated phosphorous" or "activated phosphoryl group," refers to a moiety that will provide a phosphate group when acted upon by further chemical reaction. Examples are phosphoramidites, phosphodiesters, phosphotriesters, and H-phosphonates.

The term "masked" as used herein is referring to a protecting group, which prevents a portion of a molecule from undergoing a specific chemical reaction, but is removable from the molecule following completion of that reaction as taught for example in Greene et al. "Protecting Groups in Organic Synthesis," John Wiley and Sons, Second Edition, 1991.

The term "masked" and "protecting group" are used interchangeably. As used herein, "cleave", "cleaving", "cleavage" and "deprotecting" or like terms when used herein in reference to protecting group refers to breaking a bond via which the protecting group is bound to the protected group, resulting in the cleaved protecting group and the deprotected moiety.

The term "electron-withdrawing" denotes the tendency of a substituent to attract valence electrons of the molecule for which it is part, i.e. an electron withdrawing substituent is more electronegative with respect to neighboring atoms. This is well known constant and is described in many references, for instance March, Advanced Organic Chemistry 251-9, McGraw Hill Book Company, New York, (1977). Examples of electron withdrawing groups such as halide (—Cl, —I, —F, —Br), nitro (—NO$_2$), N(alkyl)$_3$, nitrile (—CN), carbonyl-related (—C(=O, such as ketone, aldehyde, carboxylic acid, ester, amide), sulfonate (—SO$_3$H), phosphate (—PO$_4$) or a electron deficient aryl group, such as, but not limited to pyrimidine, pyrazole, imidazole.

The term "electron-donating" refers to the tendency of a substituent to repel valence electrons from neighboring atom, i.e. the substituent is less electronegative with respect to neighboring atoms. Examples of electron donating groups such as but not limited to oxide ion (—O$^-$), dialkylammonium (—N(alkyl)$_2$), alkoxide (—O(alkyl)), —S(alkyl) or an alkyl group including linear and branched, having 1 to 20 carbon atoms, cycloalkyl (including cycloalkyl having 4 to nine carbons), and the like to influence the electron density of the neighboring group to induce hydrolysis of the thiocarbonate.

The term "substituent" references a group that replaces another group in a chemical structure. Examples of substituents include non-hydrogen (e.g. halogens), functional groups (such as but not limited to amino, sulfhydryl, carbonyl, hydroxyl, alkoxy, carboxyl, silyl, silyloxy, phosphate, and the like), aryl, thioalkyl, thio, mercapto, imino, cyano, and boronyl.

"Moiety," and "group," are used interchangeably herein to refer to a portion of a molecule, typically having a particular functional or structural feature, e.g. a linking group (a portion of a molecule connecting two other portions of the molecule or molecules.)

Hyphens or dashes are used at various points throughout this application to indicate attachment, e.g. where two named groups are immediately adjacent a dash in the text, this indicates the two groups are attached to each other.

DETAILED DESCRIPTION

Several thiol-protecting groups were evaluated for their ability to cleave under mild hydrolytic conditions. Reagents for constructing the thiol groups of interest are available commercially and can be purchased, for example, from Aldrich, Sigma and so on. The compounds were constructed using methods known in the art. In the course of invention, a benzoyl thioester was evaluated first for the protection of the thiol moiety. The literature showed that this group could be easily cleaved with mild base to give the thiol and benzoate, while exhibiting good stability under acidic conditions. Unfortunately, preliminary experiments demonstrated the benzoyl thioester was too labile for selective removal of the other protecting groups.

An alternate choice was the FMOC-protecting group. However, it is documented that the by-product FMOC group (an activated alkene) can also react with the thiol group producing a very stable thioether bond.

Thirdly, the triisopropylsilyl S-protecting group (S-TIPS) was also considered. Similar in stability to the S-benzoyl group, this group was considered to be too labile, due to the weak nature of the Si—S bond. Therefore, the need remained for a more stable thiol-protecting group.

The paradigm of study is presented in Examples 1 and 2. Initial work on this synthetic route required the simultaneous removal of all protecting groups including the 3'-acetate and the β-cyanoethyl phosphate-protecting group of a single nucleotide. However, the base-induced removal of β-cyanoethyl is known to produce the carcinogen, acrylonitrile. Acrylonitrile is a Michael acceptor, which did react with the liberated thiol forming a β-cyanoethyl thioether. A precursor step was introduced to remove the β-cyanoethyl group prior to hydroxide treatment. This side reaction guided the development of the current invention.

Thiocarbonate Protecting Group

In consideration of these requirements, a thiocarbonate S-protecting group seemed to be the best candidate. Specifically, the new protecting group was the benzyloxycarbonyl group (CBz). The resonance effect of this planar functionality provides a more delocalized electrophilic site and therefore added stability as compared to the simple thioester. This group was incorporated into the synthetic scheme.

Formation of the β-cyanoethyl-protected nucleotide proceeded demonstrating that the S-CBz group could be incorporated into a nucleic acid. The subsequent steps (i.e. removal of the β-cyanoethyl group with a solution of pyridine:triethylamine:water and hydroxide treatment for the CBz and acetate groups) were high yielding procedures (>95%) with an overall yield of ~70% for the route.

To further test the cross reactivity of the S-CBz group with phosphoramidite chemistry, the S-CBz-protected thiohexanol linker phosphoramidite was synthesized from the S-CBz mercaptohexanol and the 2-cyanoethyl N,N-diisopropylamino-chlorophosphoramidite in excellent yield. Phosphorus-31 NMR provided confirmation of the formation of this product, displaying a phosphorous (III) resonance at 147.8 ppm. This demonstrated that the S-CBz protecting can be used in conjunction with phosphoramidite chemistry as a 5'-modifying reagent.

Mechanism of Cleavage

The mechanism involves nucleophilic attack of the carbonyl by the nucleophile present in solution, notably hydroxide. The resulting tetrahedral intermediate must then collapse to cause the thiol to leave. It is important to consider the relative acidities of the two leaving groups, alcohol and thiol. If the tetrahedral intermediate collapsed with the benzyl alcohol leaving, this would be energetically unflavored, as the pKa of the alkoxide (~16) is four orders of magnitude higher than that of the thiol (~12). This fact therefore, indicates that the thiol is a better leaving group.

The CBz-protected mercaptohexanol was also used for these studies.

In some embodiments, the thiol-protecting group is labile to base. However, the thiocarbonate also can be removed under acidic conditions. Strong forcing conditions (pH<1 and/or elevated temperatures) may be practiced. The mechanism may occur through protonation of the carbonyl with attack of water in a general base-type mechanism.

Deprotection Experiments

The S-CBz-protecting group was cleaved by dilute NaOH (0.5 M NaOH in aqueous 50% $CH_3OH$) but was stable towards concentrated $NH_4OH$ treatments even for prolonged periods (~18 h). Table 1 lists the deprotection conditions that were evaluated using the S-CBz-protected mercaptohexanol. Table 2 shows the susceptibilities of the electron deficient paradigm. For the fluoropyrimidine example (Example 2), the conditions were chosen because of the sensitivity of the 5-fluoropyrimidine group to nucleophilic attack. The treatment of a 5-fluorouracil (5FU) oligonucleotide (18-mer) with concentrated $NH_4OH$ at 55° C. resulted in complete decomposition of the 5FU base. Therefore, it is reasonable to believe that there is susceptibility of the S-CBz to more nucleophilic reagents (hydrazine, hydroxylamine or anhydrous methylamine) due to the sensitive nature of the 5-fluoropyrimidine toward nucleophilic attack.

The deprotection reaction of the 5'-modified nucleotide using hydroxide was performed multiple times in a variety of conditions. The pH of the reaction is changed to near neutrality by the addition of buffered phosphate. The results are summarized in the Table 3. The goal of the work was to minimize the amount of NaOH used for the reaction and thus to minimize the amount of phosphate buffer required for neutralization. In turn, this minimizes the amount of salts present in the crude reaction mixture. Moreover, this reduction in phosphate concentration helps to streamline the purification process. As shown in Table 3, a comparison of Reactions #2 and #3 clearly shows an advantage of minimizing the hydroxide used (206 equivs versus 20 equivs). The latter reaction allowed only 5% dimer formation whereas Reaction #2, with a higher concentration of hydroxide and extended reaction times, resulted in 49% dimer formation. (The dimer refers to thiol attack on the 5,6-double bond of the uridine.) Reactions were monitored until there was a complete disappearance of starting material. No other stability issues were observed with this thiol-modified nucleotide.

In that example, a possible outcome of using less NaOH would be that it would result in a slower reaction, which in theory, could lead to greater likelihood of side reactions. Conditions were found (Reaction #3) that lead to effective thiol release and minimize dimerization reactions. These results suggest that if the deprotection reaction proceeded intramolecularly, by-products could be further reduced or eliminated. The activation of the intramolecular mechanism could be induced by an orthogonal chemistry.

Non-Participating Modified Carbobenzoxy Protecting Groups

Certain structures can manipulate the electron density as measured by pKa. The ortho or para substitution of an electron-donating group to the attacking nucleophile hydroxyl would provide more electron density to make the nucleophilic attack on the thiocarbonate carbonyl. The converse would be true for an electron-withdrawing group. Example 4 describes the synthesis of an ortho-chlorobenzyloxycarbonyl derivative. The use of the 2-chlorobenzyl group demonstrates the greater susceptibility of the thiocarbonate towards hydrolysis. Table 2 provides the data towards the greater susceptibility of the 2-chloro derivative.

Intramolecularly-Assisted Cleavage

As mentioned in a previous section, the concentration of hydroxide can be important in two ways: 1) limiting the side reactions and 2) influencing reaction rate. It is reasoned though that if the nucleophile was built into the structure of the protecting group, the rate would remain constant and the need for a large amount of hydroxide would be eliminated. The neighboring group, such as, the phenolate (pKa 10), would attack the carbonyl thereby triggering the deprotection mechanism.

The liberation of the phenolate anion could be gained from orthogonal chemistry of a silyl-protecting group. Alternately, a tert-butyldimethylsilyl protecting group may function in an orthogonal fashion to provide a phenolate anion for thiocarbonate displacement.

In similar fashion, the compounds that present nucleophiles to the carbon of the carbonyl on the thiocarbonate may demonstrate on testing that an amino functionality is sufficient to deprotect the thiol despite the low reactivity of $NH_4OH$ towards the thiocarbonate. Two compounds were synthesized (i.e. Examples 5 and 6) to demonstrate the impact of nucleophilicity of the attacking nucleophile. It is commonly known that there is a large difference in the pKa of the amino groups on alkyl carbons and aryl carbons. Typically, amino groups on anilines have pK's around 5, where an alkyl amine would have a pKa about 10. This difference can have a measurable effect on the rate of the reaction. Example 5 describes the synthesis of a 2-[(benzyloxycarbonyl)amino] ethoxycarbonyl-mercaptohexanol (ZEHS6OH). Example 6 describes the synthesis of a 2-[N-(benzyloxycarbonyl)-aminobenzyloxycarbonyl)]-mercaptohexanol (ZBHS6OH). After conversion to a phosphoramidite (Example 9) and added to the 5'-end of an oligonucleotide, the neighboring amino group facilitated intramolecular cleavage of the thiocarbonate upon hydrogenolysis of the carbamate moiety.

An intramolecular amino group would increase the rate of the hydrolysis substantially due to the proximity and orientation of the amino group. This intramolecular effect is related to a term used in catalysis called Effective Molarity (EM). The EM is defined as the concentration of the reactive group required to make the intermolecular reaction go at the observed rate of the intramolecular process. This principle could be applied here to protection group chemistry. An explanation therefore of the low reactivity of $NH_4OH$ could be that the attacking nucleophile may not have sufficient effective concentration to increase the rate over the observed time period.

Related structures could further aid in the optimization of the thiocarbonate S-protecting group. The influences of the EM can result by restricting the movement of the liberated amino group through the presence of the exocyclic FMOC-protected amine on the dioxane ring. Lastly, a 3-(dimethoxytrityl)-serinol derivative or an FMOC-amino-2-tetrahydropyran derivative can be used, which upon unmasking, the primary hydroxyl group or primary amino group induces hydrolysis. Modifications of this type would be useful for oligonucleotides with internal thiol groups or branched analogs. An immediate benefit would be that the bulky DMT group would improve purification on a reversed phase column.

Suitable thiocarbonates that can be used in the practice of the instant invention include a compound of formula where the sulfur is covalently attached to a carbon through a thiocarbonate group. An example is:

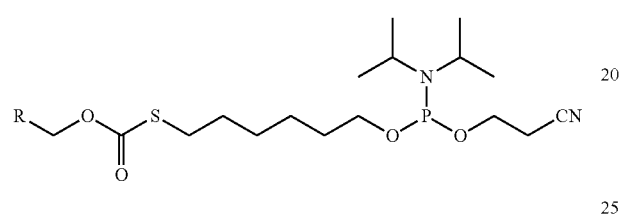

wherein R is an aromatic or aliphatic moiety. In one embodiment, R is an unsubstituted phenyl ring. This compound is prepared through two steps. Step 1 involves the synthesis of the thiocarbonate linker (Examples 3, 4, 5, 6). The linker is assembled by the action of either a chloroformate or p-nitrophenyl carbonate on the mercaptohexanol. After appropriate drying of this linker by molecular sieves, the hydroxyl moiety of the thiocarbonate linker reacts with an activated beta-cyanoethyl protected phosphite (Example 9). Once prepared, the resulting phosphoramidite as shown above, is reacted with the 5'-terminal of an oligonucleotide. The procedure for this modification of the 5'-terminus is well known in the synthetic production of DNA field. In brief, the phosphoramidite as shown above, is activated for coupling by the treatment with tetrazole or similar reagents such as 5-ethylthio-1H-tetrazole (ETT). After coupling (usually a few minutes), the phosphorous (III) atom is oxidized by the action of an iodine solution to phosphorous (V). The product is a thiocarbonate-linked linker that employed a phosphotriester as the linkage group. The deprotection studies ensued.

While any aryl or heteroaryl would be applicable, suitable examples of aryl and heteroaryl moieties, which comprise B of the formula, include:

A)

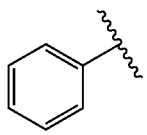

B)

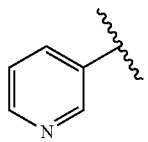

C)

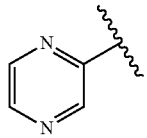

D)

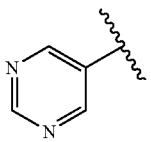

E)

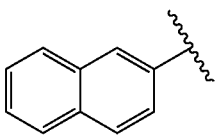

F)

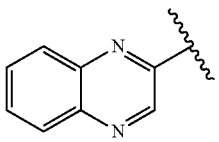

G)

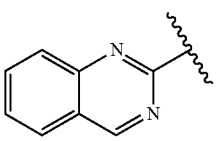

H)

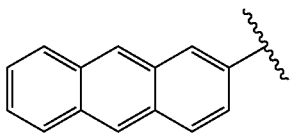

I)

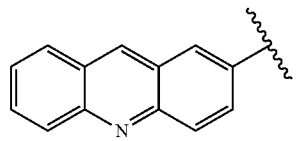

J)

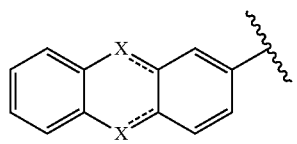

K)

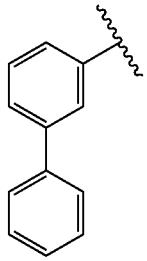

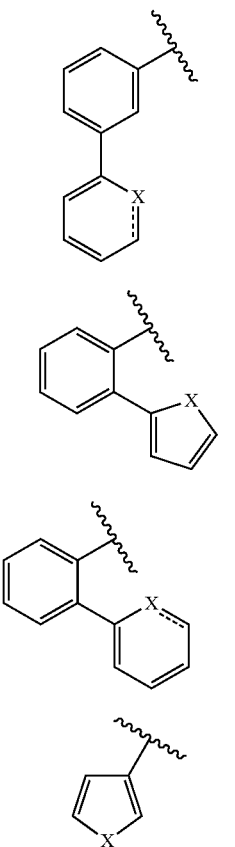

where X is O, S, or NH and where these examples of the moiety denoted as R would be obtained as the substituted methyl alcohol form (as in the case of the exemplified compound above, a benzyl alcohol is used). Further, as noted in the examples (specifically Examples 5 and 6), the conversion of the alcohol to a para-nitrophenyl carbonate would ensue through the use of the para-nitrophenyl chloroformate in non-aqueous solutions of pyridine and dichloromethane. The para-nitrophenyl carbonate derivative is then ready to react with mercaptohexanol to give the material ready for the conversion to the phosphoramidite. Standard phosphoramidite synthesis would ensue using literature-based methods. Example 9 teaches how this can be accomplished.

Suitable alkyl moieties include, alkyl or alkenyl moieties, branched, cyclic or linear from 1 or 2 to about 20 carbons in size.

In certain embodiments, the aromatic moiety is substituted with one or more electron withdrawing groups, such as, halide (—Cl, —I, —F or —Br), nitro (—NO$_2$), N(alkyl)$_3$, nitrile (—CN), carbonyl-related (—C(=O), or sulfonate (—SO$_3$H), or electron-donating groups, such as, oxide ion (—O$^-$), dialkylammonium (—N(alkyl)$_2$), alkoxide (—O(alkyl)), an acylated amine in the form of a carbamate, such as, carbobenzoxycarbonyl (CBz) or fluorenyloxycarbonyl (FMOC) or fluorenyloxy-carbonyl derivative or alkyl-substituted, such as, ethyl derivative such as 2,2,2-trihaloethyl, 2-trimethylsilylethyl, acetyl or haloacetyl or photolytically cleaved, such as, m-nitrophenyl, or urea-type, such as, phenothiazinyl-10-carbonyl, N-sulfenyl, N-sulfonyl, N-phosphinyl, N-nitro, or an imine based group, such as, N-[2-(trimethylsilyl)ethoxy]methyl group, or an alkyl group to influence the electron density of the neighboring group to induce hydrolysis of the thiocarbonate.

In one embodiment, a thiocarbonate of interest has the following structure:

and in one embodiment, R$_1$=R$_2$=R$_3$=R$_4$=X=H. Alternately, R$_{1-4}$ can comprise a series or a combination of electron withdrawing and/or electron donating groups. As one skilled in the art could arrange, R$_1$ through R$_4$ would be placed to influence (increase or decrease) the nucleophicity of the X group. X would be a chemically masked nucleophile, which when acted upon a chemical reagent liberates a nucleophile, such as, amine, hydroxyl, or thiol groups.

As prepared in Examples 5 and 6, X could be a masked amine, where the amino group is protected with a carbamate such as carbobenzoxycarbonyl (CBz) or fluorenyloxycarbonyl (FMOC) or fluorenyloxycarbonyl derivative or alkyl-substituted such as ethyl derivative such as 2,2,2-trihaloethyl, 2-trimethylsilylethyl, acetyl or haloacetyl or photolytically cleaved such as m-nitrophenyl, or urea-type such as phenothiazinyl-10-carbonyl, N-sulfenyl, N-sulfonyl, N-phosphinyl, N-nitro, or an imine based group such as N-[2-(trimethylsilyl)ethoxy]methyl group.

The nucleophile can be an oxygen, such as, in the form of an aryloxides, such as, phenolate, naphtholate, anthracenolate, imidazolate, pyridylolate, pyrimidylolate, and biphenolates. Alternately, a saturated or unsaturated alkoxide of 1 to 20 carbons in size, either branched or linear can be used.

The hydroxyl functionality of X could be masked through the use of substituted methyl ether, such as, t-butylthiomethyl, benzyloxymethyl, siloxymethyl, bis(2-chloromethoxy)methyl, 2-methoxymethyl, tetrahydropyranyl and tetrahydrofuranyl or substituted ethyl ethers, such as, 1-ethoxy, 1-methyl-1-benzyloxymethyl, 2-trimethylsilylethyl, 2,2,2-trihaloethyl, allyl, and benzyl, or substituted benzyl ethers, or silyl ethers, such as, triisopropylsilyl, diethylisopropylsilyl, t-butyldimethylsilyl, and diphenylmethylsilyl, or esters, such as, formyl, acetyl, haloacetyl, levulinyl, phenoxyacetyl, pivoloyl, adamantyl, and benzoyl, or carbonates, such as, 9-fluorenylmethyl, ethyl, haloethyl, 2-(trimethylsilyl)ethyl, 2-(phenylsulfonyl)ethyl, vinyl, allyl, p-nitrophenyl, benzyl, and methyl dithiocarbonate, or assisted cleavage groups, such as 2-iodobenzoate, 4-azidobutyrate, 2-formylbenzenesulfonate, and 2-(methylthiomethoxymethyl)benzoate, or sulfonates, such as, O-sulfate, O-mesylates, O-benzylsulfonate, and O-tosylate.

The nucleophile can be a sulfur, for example, in the form of a sulfide, such as, phenylsulfide, naphthylsulfide, anthracenylsulfide, imidazylsulfide, pyrrolylsulfide, pyridylsulfide, pyrazinylsulfide, pyrimidylsulfide, and biphenolsulfide. Alternately, a saturated or unsaturated alkenylsulfide or alkylsulfide of 1 to 20 carbons in size, either branched or linear, can be used.

The thiol functionality of X could be masked through the use of substituted thioethers, such as, S-benzyl, S-p-methoxybenzyl, S-4-picolyl, or substituted methylthio ethers, such as, S-anthrylmethyl, S-ferrocenylmethyl, S-methoxymethyl, S-2-tetrahydropyranylS-benzylthiomethyl, thiazolidines, S-acetylmethyl, S-carboxymethyl, and S-cyanomethyl, or substituted S-ethyl ethers, such as, 2-nitro-1-phenylethyl, 2-cyanoethyl, and 2-phenylsulfonylethyl, or thioesters, such as, S-acetyl, S-benzoyl and N-t-butoxycarbonyl)-N-methyl-γ-aminobutyrate, or unsymmetrical disulfides, or S-sulfenyl groups, or S-phosphino derivatives, such as, S-(diphenylphosphino)thioyl.

Oligonucleotide 5'-Modifications:

This protecting group strategy is applicable to the synthesis of 5'-thiol oligonucleotides. Due to the sensitivity of the thiocarbonate group to hydroxide ion at elevated temperatures, alternate schemes aside from standard methods of deprotection (NH₄OH at 55° C.) might be used if final deprotection of the thiocarbonate were required.

The oligonucleotide can refer to a nucleotide protected, for example, by an UltraMILD chemistry (Glen Research) protecting group. Similarly, the facile cleavage of the oligonucleotide from solid controlled pore glass (CPG) would ensue. For this liberation from the solid phase, UltraMILD or Universal Support III (Glen Research) would be acceptable. According to the product's protocol, cleavage is carried out with a variety of reagents, including methanolic potassium carbonate (50 mM) in 50% methanol/water (v/v) for up to 4 hours but most notably for this strategy would be the use of ammonium hydroxide at room temperature for up to 2 hours (Table 2: stability for up to 18 hours was observed with ZS6OH).

A DNA or RNA molecule would be synthesized in an automated oligonucleotide synthesizer or in solution with the appropriate reagents for phosphoramidite or phosphodiester nucleic acid synthesis. Standard automated methods could be employed. The invention can find use with known automated oligonucleotide synthesis schemes, such as, when using Ultra-Mild reagents and Ultra-Mild CPG supports.

Hence, the compounds of interest find use in any oligonucleotide synthesis scheme, practicing the materials and methods as taught, and including the protecting group of interest. Removal of the compound of interest can be as taught herein or using any of the materials and methods provided in the oligonucleotide synthesis schemes, provided the conditions taught herein are considered.

The deprotected oligonucleotide comprises a reactive sulfhydryl or thiol group. That group provides a means for the ready joining of the oligonucleotide of interest to any of a variety of other entities, such as, a compound on a solid phase, a targeting moiety to direct the oligonucleotide to a particular site, to a carrier, such as, a molecular carrier, wherein said oligonucleotide has a therapeutic use, such as, an siRNA and so on, using standard chemistries, such as, forming a disulfide bond on oxidation.

The invention now will be exemplified in the following non-limiting examples.

EXAMPLES

Example 1

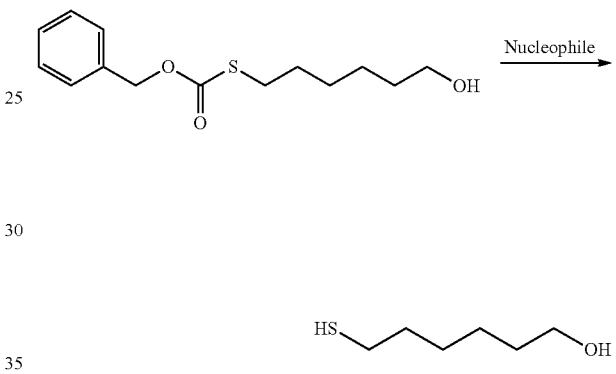

TABLE 1

Carbobenzoxycarbonyl Thiocarbonate Stability Studies Under Basic Conditions

| Nucleophilic Conditions | Time Points (min) | Temp | Half-life | Technique | Comment |
| --- | --- | --- | --- | --- | --- |
| 0.5M NaOH 50% CH₃OH/H₂O | 0, 30, 75 | rt | 17 min | HPLC | Complete deprotection |
| Conc. NH₄OH (neat) | 0, 10, 120, 180, 1080 | rt | n/a | tlc | un-effected after 18 h |
| NH₄OH/iPrOH (50/50 v/v) | 0, 30, 60, 180 | rt | n/a | tlc | significant amount thiocarbonate material present afer 3 h |
| 0.1 N NaOCH₃/CH₃OH | 0, 20, 90, 120, 1440 | rt | n/a | tlc | slow deprotection - complete deprotection after 24 h | iPrOH is isopropyl alcohol, rt is room temperature (~22° C.), tlc is thin layer chromatography (purchased from Merck)

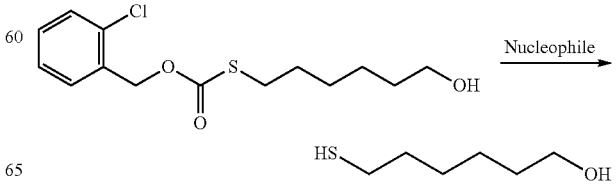

TABLE 2

Effect of Electron-Withdrawing group (i.e. ortho-Chlorine) on the Phenyl Ring.

| Nucleophilic Conditions | Time Points (min) | Temp | Cleavage Percent | Technique | Comment |
|---|---|---|---|---|---|
| NH$_4$OH (conc) | 1080 | rt | 50 | HPLC | Significant degradation |
| 0.1M NaOH | 60 | rt | 85 | HPLC | Significant degradation |
| Pyridine | 1440 | rt | n/a | HPLC | un-effected after 18 h |
| CH$_3$OH | 1440 | rt | n/a | HPLC | un-effected after 18 h |
| Methanolic K$_2$CO$_3$ | 80, 240, 1320 | rt | 35 | HPLC | modest degradation | rt is room temperature (~22° C.), tlc is thin layer chromatography (purchased from Merck), Cleavage Percent is reflective of longest time period.

Example 2

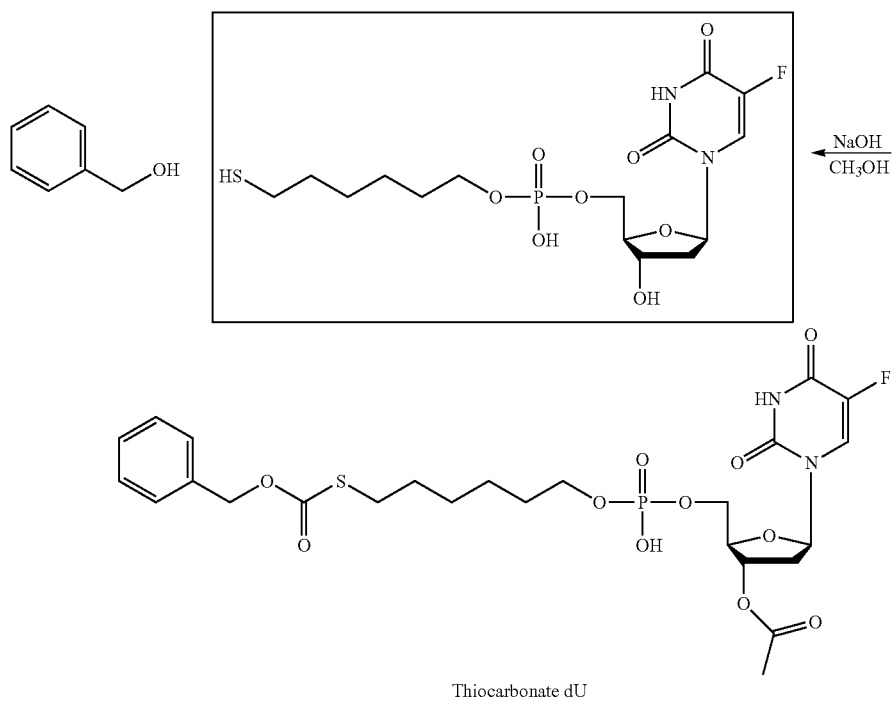

Thiocarbonate dU

The table below presents data for the NaOH induced hydrolysis of the Thiocarbonate deoxyuridine (dU). The reactions were carried out at room temperature (~22° C.). The columns starting from the left to the right: Thiocarbonate dU amounts are presented in the column identified as, "Scale," in micromoles; initial micromolar concentration prior to the addition of the NaOH; the amount of NaOH used in number of molar equivalents and final in-solution concentration used; the overall time of the reaction; the percentage of dimer found (see note below table); the reaction is quenched by adding sodium phosphate to the deprotection reaction, the final PO$_4$ concentration is critical for ease of purification (low PO$_4$ conc makes it easier to purify by HPLC); the final pH of the reaction is provided; and in the right-most column, the final concentration of nucleotide (dU) in solution is provided.

TABLE 3

| Reaction # | Thiocarbonate dU (umol) | Initial dU (µM) | # eq NaOH | NaOH Conc. (M) | Time (h) | % dimer | Final PO4 (µM) | final pH | Final dU conc (µM) |
|---|---|---|---|---|---|---|---|---|---|
| 1 | 242 | 2.4 | 207 | 0.5 | 1 | n.a | 333 | 7.3 | 0.8 |
| 2 | 8.49 | 2.4 | 206 | 0.5 | 23 | 49 | 333 | 7 | 0.8 |
| 3 | 25 | 5 | 20 | 0.1 | 2.5 | 5 | 66 | 7.1 | 1.67 |
| 4 | 66.8 | 5 | 20 | 0.1 | 3 | 8.5 | 100 | 7.2 | 2.5 |
| 5 | 77.9 | 5 | 10 | 0.05 | 5 | 15.3 | 144 | 7 | 3.5 |
| 6 | 77.9 | 10 | 10 | 0.1 | 2.75 | 9.1 | 143 | 7.3 | 7.1 |

Note:
% Dimer refers to amount of inter-molecular Michael reaction at the 5-position of the uridine ring - a characteristic that specific to this particular example.

Example 3

6-(S-Carbobenzoxy)-mercaptohexanol (ZS6OH)

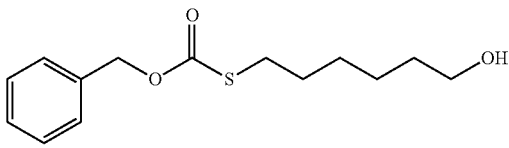 [SMILES: O=C(OCc1ccccc1)SCCCCCCO]

A solution containing 1 mL (7.31 mmoles, 0.981 g/mL) of 6-mercapto-1-hexanol (Aldrich) in a solution of 20 mL of aqueous 1 M $Na_2CO_3$ and 20 mL of tetrahydrofuran was treated with 1.6 mL (10.45 mmoles, 1.195 g/mL) of benzyl chloroformate (Aldrich). The solution was stirred for 2 h, and then poured onto $CHCl_3$ (~100 mL). The layers were separated, and the aqueous layer was re-extracted with $CHCl_3$ (2×50 mL). This material was purified by flash chromatography (150 g silica gel, 230-400 mesh; packed with 30% ethyl acetate in hexanes; silica gel TLC $R_f$ 0.33 (30% ethyl acetate in hexanes), yield 1.79 g (6.669 mmoles), 91%; $^1$H NMR ($CDCl_3$): δ 1.40-1.69 (m, 8H, N—$CH_2$—$CH_2$—$CH_2$—$CH_2$—$CH_2$—$CH_2$—OH), 2.90 (t, J=7.14 Hz, 2H, S—$CH_2$—$CH_2$—$CH_2$—$CH_2$—$CH_2$—$CH_2$—OH), 3.66 (m, 2H, S—$CH_2$—$CH_2$—$CH_2$—$CH_2$—$CH_2$—$CH_2$—OH), 5.25 (s, 2H, benzyl $CH_2$), 7.39 (m, 5H, phenyl H).

Example 4

Synthesis of C1ZS6OH

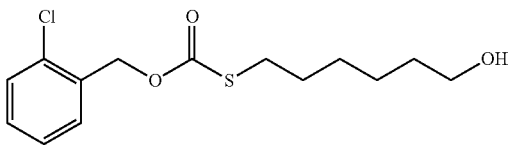 [SMILES: O=C(OCc1ccccc1Cl)SCCCCCCO]

A solution containing 3 g (22.17 mmoles, 0.981 g/mL) of 6-mercapto-1-hexanol (Aldrich) was dissolved in a solution of 150 mL of aqueous 1 M $Na_2CO_3$ and 150 mL of tetrahydrofuran was treated with 3.86 mL (24 mmoles, 1.335 g/mL) of 2-chlorobenzyl chloroformate (Aldrich). The solution was stirred for 4 h, and then poured onto $CHCl_3$ (~100 mL). The layers were separated, and the aqueous layer was re-extracted with $CHCl_3$ (2×50 mL). This material was purified by flash chromatography (150 g silica gel, 230-400 mesh; packed with 10% ethyl acetate in hexanes; silica gel TLC $R_f$ 0.375 (40% ethyl acetate in hexanes), yield 5.1 g, 75%; $^1$H NMR ($CDCl_3$): δ 1.35-1.71 (m, 8H, N—$CH_2$—$CH_2$—$CH_2$—$CH_2$—$CH_2$—$CH_2$—OH), 2.89 (t, J=7.14 Hz, 2H, S—$CH_2$—$CH_2$—$CH_2$—$CH_2$—$CH_2$—$CH_2$—OH), 3.64 (m, 2H, S—$CH_2$—$CH_2$—$CH_2$—$CH_2$—$CH_2$—$CH_2$—OH), 5.35 (s, 2H, benzyl $CH_2$), 7.27-7.44 (m, 4H, phenyl H).

Example 5

Synthesis of ZEHS6OH

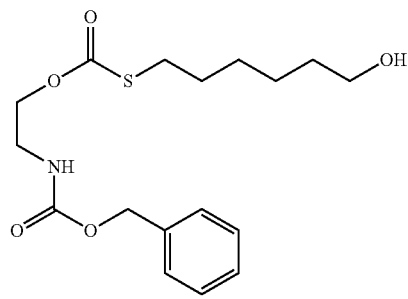 [SMILES: O=C(NCCOC(=O)SCCCCCCO)OCc1ccccc1]

A solution of ethanolamine (4 g, 65.48 mmoles, Aldrich) in 10% $Na_2CO_3$ aqueous solution and 100 mL of tetrahydrofuran (THF) was treated with benzyl chloroformate (11.5 mL, 1.5 equivalents, 13.7 g) at room temperature for 24 h. The reaction was then concentrated to a thick oil. The oil was taken up in $CHCl_3$ and washed with 1 M HCl. The organic phase was taken and dried over $Na_2SO_4$. The product was crystallized from hot hexanes, yield 10 g, 78.3%; $^1$H NMR ($CDCl_3$): δ 3.52 (q, J=7.14 Hz, 2H, N—$CH_2$—$CH_2$—OH), 4.36 (t, J=7.14 Hz, 2H, N—$CH_2$—$CH_2$—O), 5.18 (s, 2H, benzyl $CH_2$), 7.35 (m, 5H, phenyl H)

A round bottom flask (250 mL) was joined to a reflux condenser and charged with the reactants under nitrogen. The N-CBz ethanolamine (6.6 g, 33.8 mmoles) was dissolved in 3 mL of dry pyridine and the para-nitrophenyl chloroformate (6.88 g, Aldrich) in 5 mL of $CH_2Cl_2$ was added slowly (over 20 min). The temperature did rise slightly and the reaction was stirred for 2 h. The solution was then poured on to 0.5 M HCl (150 mL) and the $CH_2Cl_2$ layer diluted to 50 mL with fresh $CH_2Cl_2$. The organic layer was drained off and dried over anhydrous $Na_2SO_4$, yield 9.3 g, 76.3%; $^1$H NMR ($CDCl_3$): δ 3.57 (q, J=7.14 Hz, 2H, N—$CH_2$—$CH_2$—O), 4.35 (t, J=7.14 Hz, 2H, N—$CH_2$—$CH_2$—O), 5.13 (s, 2H, benzyl $CH_2$), 7.39 (m, 7H, phenyl H), 8.25 (d, J=6.9 Hz, 2H, phenyl H).

An aliquot of para-nitrophenylcarbonate derivative above (4.6 g, 12.7 mmoles) was dissolved in 50 mL of dioxane and mixed with 100 mL of 1 M $Na_2CO_3$ aqueous solution and 1.5 mL of 6-mercaptohexanol (10.9 mmoles, Aldrich) at room temperature. The solution was warmed to 30° C. for 16 h. Afterwards, the solution was concentrated under reduced pressure and diluted with 300 mL of water. The aqueous phase was extracted three times with 150 mL $CHCl_3$. The organic layers were pooled and washed 4 times with 250 mL water (until the yellow color disappeared). The organic layer was then dried with anhydrous $Na_2SO_4$ and concentrated. This material was purified by flash chromatography (150 g silica gel, 230-400 mesh; packed with 50% ethyl acetate in hexanes; silica gel TLC $R_f$ 0.25 (50% ethyl acetate in hexanes), yield 2.86 g (6.86 mmoles), 63%; $^1$H NMR ($CDCl_3$): δ 1.38-1.72 (m, 8H, N—$CH_2$—$CH_2$—$CH_2$—$CH_2$—$CH_2$—$CH_2$—OH), 2.87 (t, J=7.14 Hz, 2H, S—$CH_2$—$CH_2$—$CH_2$—$CH_2$—$CH_2$—$CH_2$—OH), 3.48 (q, J=7.14 Hz, 2H, N—$CH_2$—$CH_2$—OH), 3.64 (m, 2H, S—$CH_2$—$CH_2$—

CH$_2$—CH$_2$—CH$_2$—CH$_2$—OH), 4.28 (t, J=7.14 Hz, 2H, N—CH$_2$—CH$_2$—O), 5.10 (s, 2H, benzyl CH$_2$), 7.35 (m, 5H, phenyl H).

Example 6

Synthesis of ZBHS6OH

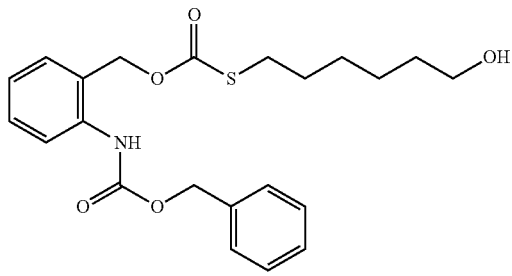 [SMILES: O=C(Nc1ccccc1COC(=O)SCCCCCCO)OCc1ccccc1]

Five grams (40.6 mmoles) of 2-aminobenzyl alcohol (Aldrich) was dissolved in 200 mL of anhydrous dioxane and treated with 100 mL of 1 M Na$_2$CO$_3$ aqueous solution. To this mixture benzyl chloroformate (8 mL) was added. The mixture was stirred overnight (~16 h) and then poured onto 100 mL CHCl$_3$. This organic phase was washed with 1 M HCl to remove any unreacted starting material. The layers were separated and the organic phase was dried with anhydrous Na$_2$SO$_4$. The solution was filtered through filter paper and the product re-crystallized using hexanes to yield a white crystalline solid, yield 5.23 g, 50%; %; $^1$H NMR (CDCl$_3$): δ 4.67 (s, 2H, benzyl CH$_2$), 5.20 (s, 2H, benzyl CH$_2$), 7.00-7.43 (m, 9H, phenyl H), 7.972 (br d, J=8.14 Hz, OH and NH).

This material produced was used directly for the next experiment. The 2-(N-CBz-amino)-benzyl alcohol (0.36 g) was dissolved in a solution containing 600 μL of pyridine. This solution was added slowly to the para-nitrophenyl chloroformate (pNCl) solution in dichloromethane (DCM) (0.28 g of pNCl formate in 10 mL). The reaction was stirred for 2 h, then extracted over 0.5 M HCl (50 mL). The CH$_2$Cl$_2$ layer was dried over Na$_2$SO$_4$, yield 0.42 g (54%).

An aliquot of para-nitrophenyl carbonate derivative above (0.42 g, 1 mmole) was dissolved in 6 mL of CH$_2$Cl$_2$ and mixed with 1 mL of 1 M Na$_2$CO$_3$ aqueous solution and 120 μL of 6-mercaptohexanol (0.88 mmoles, Aldrich) at room temperature. The solution was warmed to 30° C. for 16 h. Afterwards, the solution was concentrated under reduced pressure and diluted with 300 mL of water. The aqueous phase was extracted three times with 20 mL CHCl$_3$. The organic layers were pooled and washed 4 times with 10 mL water (until the yellow color disappeared). The organic layer was then dried with anhydrous Na$_2$SO$_4$ and concentrated. This material was purified by flash chromatography (50 g silica gel, 230-400 mesh; packed with 50% ethyl acetate in hexanes; silica gel TLC R$_f$ 0.5 (50% ethyl acetate in hexanes), yield 0.42 g (1 mmole), 71%; $^1$H NMR (CDCl$_3$): 1.38-1.72 (m, 8H, N—CH$_2$—CH$_2$—CH$_2$—CH$_2$—CH$_2$—CH$_2$—OH), 2.87 (t, J=7.14 Hz, 2H, S—CH$_2$—CH$_2$—CH$_2$—CH$_2$—CH$_2$—CH$_2$—OH), 3.63 (m, 2H, S—CH$_2$—CH$_2$—CH$_2$—CH$_2$—CH$_2$—CH$_2$—OH), 5.10 (s, 2H, benzyl CH$_2$), 7.00-7.43 (m, 9H, phenyl H).

Example 7

CBz-CE-5FdU Triester

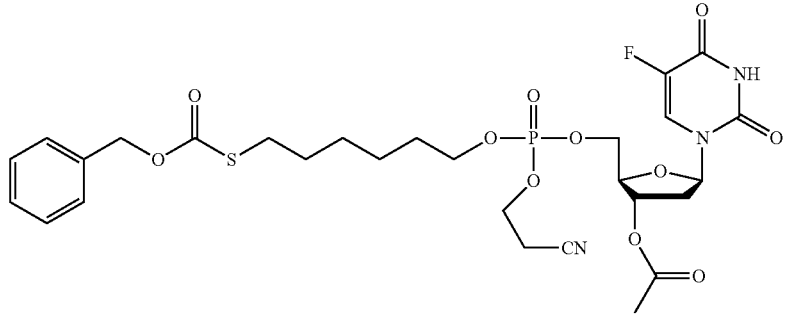

A suspension of 3'-O-acetyl-5-fluoro-2'-deoxyuridine (100 mg, 0.347 mmole) and diisopropylaminotetrazolium salt (62.4 mg, 0.36 mmole) in 1.0 mL of anhydrous CH$_3$CN (Glen Research Amidite Diluent) was treated dropwise with 2-cyanoethyl tetraisopropylphosphoramidite (96 mg, 0.315 mmole) and stirred for 3 h at room temperature. $^{31}$P NMR (benzene-d) was used to monitored the reaction's progress and identify the product. The reaction mixture was then concentrated to dryness to give a white oily solid. This product was used immediately for the next step without further purification.

A solution of tetrazole in CH$_3$CN (2 mL, 0.9 mmoles tetrazole (0.45 M)) was added to the phosphite above, followed by the addition of 6-(S-carbobenzoxy)-mercaptohexanol (91 mg, 0.34 mmoles). The reaction mixture was stirred for 3 h, then titrated with oxidizing solution (required 10 mL of 0.02 M I$_2$ in aqueous pyridine (72 mg I$_2$ in 13:1:0.2 parts tetrahydrofuran:H$_2$O:pyridine (14.2 mL final volume)). Upon retention of the yellow color, the solution was poured onto CHCl$_3$ (100 mL) and H$_2$O (80 mL). The organic layer was separated, dried (Na$_2$SO$_4$) and concentrated to a colorless oil. Analysis by thin layer chromatography (tlc) (see below for description) showed no 6-(S-carbobenzoxy)-mercaptohexanol present. Purification of the product was accomplished by silica gel flash chromatography (28 g, packed with 10% hexanes in ethyl acetate, sample in CHCl$_3$) and eluted with 10% hexanes in ethyl acetate. Fractions containing the product as identified by thin layer chromatography (glass-backed silica gel, R$_f$ 0.28 (10% hexanes in ethyl acetate))

were pooled and concentrated to dryness under diminished pressure, yield 108 mg (46%); $^{31}$P NMR (CDCl$_3$): δ −0.225 phosphorous (V) phosphotriester; $^1$H NMR (CDCl$_3$): δ 1.38-1.70 (m, 8H, N—CH$_2$—CH$_2$—CH$_2$—CH$_2$—CH$_2$—OH), 2.02 (s, 3H, OC—CH$_3$), 2.17 (m, 1H, deoxyribose 2'-H), 2.46 (m, 1H, deoxyribose 2'-H), 2.76 (t, J=6 Hz, 2H, NC—CH$_2$—CH$_2$—), 2.84 (t, J=7.6 Hz, 2H, S—CH$_2$—CH$_2$—CH$_2$—CH$_2$—CH$_2$—CH$_2$—OH), 4.075-4.384 (m, 7H, NC—CH$_2$—CH$_2$—; S—CH$_2$—CH$_2$—CH$_2$—CH$_2$—CH$_2$—CH$_2$—O, deoxyribose 5'-H, and deoxyribose 4'-H), 5.21 (s, 2H, phenyl CH$_2$), 5.35 (d, 1H, deoxyribose 3'-H), 6.315 (t, 1H, deoxyribose 1'-H), 7.42 (s, 5H, phenyl on CBz group), 7.74 (d, J=6.79 Hz, H-6).

Example 8

Synthesis of Diester

Deprotection of 5FdU Triester

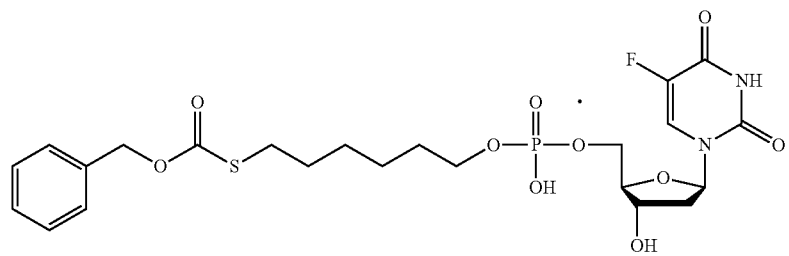

A sample of the triester of Example 7 (10.8 g, 16.10 mmoles) was dissolved in 322 mL of a solution consisting of pyridine, triethylamine and H$_2$O (25 mL/8.4 mU 8.4 mL, respectively; total volume 41.8 mL). The solution was incubated at room temperature for 120 min, and then concentrated under reduced pressure on a rotovap. The residue was then re-dissolved in 400 mL of a 1:1 (v/v) solution of CH$_3$OH in H$_2$O, and concentrated to near dryness. The residue was then analyzed by HPLC using a linear gradient of 0.1 M ammonium acetate in CH$_3$CN (Rainin MicroSorb MV column 4.6 mm×150 mm; gradient: 0 to 100% CH$_3$CN over 30 min; flow rate 1.0 mL/min; UV monitored at 260 nm). The product eluted at 16.5 min under these conditions. Analysis by silica gel tlc using a solvent mixture of CHCl$_3$/CH$_3$OH/H$_2$O (50 mL/20 mL/2.5 mL) revealed the absence of the starting triester (no spot for the triester using 10% hexanes in ethyl acetate, but only baseline material) and the clean conversion to the phosphodiester within 30 min (R$_f$ 0.65 (CHCl$_3$/CH$_3$OH/H$_2$O (50 mL/20 mL/2.5 mL)); $^{19}$F NMR (CD$_3$OD): δ −169.03 (d, J=5.6 Hz, F—H coupling); isolated yield quantitative 9.96 g; NMR (CD$_3$OD): δ 1.395-1.98 (m, 8H, N—CH$_2$—CH$_2$—CH$_2$—CH$_2$—CH$_2$—CH$_2$—OH), 2.07 (s, 3H, OC—CH$_3$), 2.36 (m, 2H, deoxyribose 2'-H), 2.84 (t, J=7.6 Hz, 2H, S—CH$_2$—CH$_2$—CH$_2$—CH$_2$—CH$_2$—CH$_2$—OH), 3.89 (m, 2H, S—CH$_2$—CH$_2$—CH$_2$—CH$_2$—CH$_2$—CH$_2$—O), 4.11 (m, 2H, deoxyribose 5'-H), 4.2 (s, 1H, deoxyribose 4'-H), 5.21 (s, 2H, phenyl CH$_2$), 5.35 (s, 1H, deoxyribose 3'-H), 6.29 (t, J=6.8 Hz, 1H, deoxyribose 1'-H), 7.34 (s, 5H, phenyl on CBz group), 8.07 (d, J=6.4 Hz, H-6).

Example 9

6-(S-Carbobenzoxy)-mercaptohexyl-2-cyanoethyl N,N',N,N'-tetraisopropylphosphoramidite

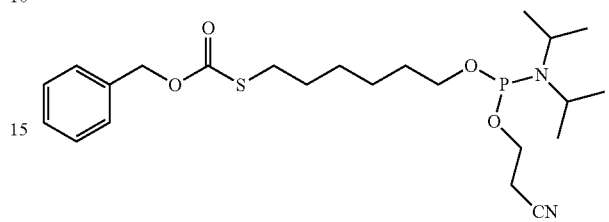

In this example, the ZS6OH is used. A solution of 6-(S-carbobenzoxy)-mercaptohexanol (ZS6OH) (1.08 g, 4 mmoles) in 10 mL dry benzene was treated with 587 uL of triethylamine and cooled to 0° C. in an ice bath. This mixture was then treated with 1 g of 2-cyanoethyl N,N-(diisopropylamino)-chlorophosphoramidite in 10 mL of dry benzene. The mixture was allowed to warm to room temperature with stirring for 2 h. $^{31}$P NMR (benzene-d6) was used to monitor the reaction's progress and identify the product. The reaction mixture was then concentrated to give a colorless oily liquid. This product was used immediately for the next step without further purification, yield>95%. If necessary, purification was by silica gel flash chromatography using 1% triethylamine in ethyl acetate hexane (1 to 3 parts by volume). The procedure was performed with C1ZS6OH, ZEHS6OH, ZBHS6OH.

Example 10

Synthesis of Oligonucleotide using 6-(S-Carbobenzoxy)-mercaptohexyl-2-cyanoethyl N,N'-diisopropylphosphoramidite (S-CBz 5'-Modifier) and UltraMild Chemistry The modified oligomer (250 nmole scale) was synthesized on a Millipore Expedite or equivalent solid phase DNA/RNA synthesizer, using corresponding Ultra-Mild phosphoramidites from a commercial source (Glen Research) or synthesized. Ultra-Mild controlled pore glass (CPG, 20-5010-xx, Glen Research) was used. UltraMild Cap A mix was also used as to facilitate the deprotection. Isopropylphenoxyacetyl anhydride was used in the Cap A Mix. UltraMild Oligonucleotide Chemistry is trademarked by Glen Research. The S-CBz 5'-modifier linker was then introduced into the oligomer by coupling a 6-(S-carbobenzoxy)-mercaptohexyl-2-cyanoethyl N,N'-diisopropylphosphoramidite (S-CBz 5'-modifier) synthon (synthesis as in Example 9) and added to the oligonucleotide using phosphoramidite chemistry at the final coupling step of the solid phase synthesis. When necessary, the sulfuring agent, 3H-1,2-benzodithiole-3-one-1,1-dioxide (Beaucage reagent, Glen Research) was substituted for the low moisture oxidizer to effect sulfurization of the phosphite to give the phosphorothioate according to standard established procedures.

The 5'-modified oligomer (i.e. 5'-CBz-S-alkyl-p-AGTCG-TAGCTAGCCAGCATT, where the CBz-S-alkyl linker was attached through a phosphate at the 5' terminus) was deprotected and removed from the solid support using 0.05 M $K_2CO_3$ in 50% (v/v) $CH_3OH$ in $H_2O$ for up to 4 hours. The potassium carbonate could be neutralized with cooling using 6 uL of glacial acetic acid per milliliter of potassium carbonate and analyzed directly. Alternately, the modified oligonucleotide was purified using a SepPak (20 cc). The SepPak cartridge was pre-equilibrated with $CH_3OH$ (30 mL), 50% (v/v) $CH_3CN$ in $H_2O$, and then $H_2O$. The potassium carbonate solution containing the oligonucleotide was diluted to 100 mL with 0.5 M $Na_xPO_4$ (pH 5.8) and applied to the pre-equilibrated SepPak™ cartridge. The column/cartridge was washed with $H_2O$, then a 5% $CH_3CN$ in $H_2O$ to elute the failed sequences. (Failed sequences are any sequence that is not the complete sequence as mentioned.) It should be noted that if the yield of the full-length oligonucleotide is low, one should examine this fraction for product resulting from premature loss of the dimethoxytrityl group (DMT). To remove the $CH_3CN/H_2O$ mixture from the column, a $H_2O$ wash was performed (30 mL). This step was accomplished by the elution with an aqueous solution of trifluoroacetic acid (1% solution)(~30 mL). The column became orangish in color due to the presence of the DMT cation. After 10 min of stopped flow, the column was then flushed with $H_2O$ and 2 mL of 0.5 M $Na_xPO_4$ (pH 5.8). The column was once again washed with $H_2O$ to remove any residual buffer and trifluoroacetic acid. The product was then eluted with 50% $CH_3CN$ in $H_2O$.

Final purification of the product was carried out on a reverse phase C18 column using a linear gradient of $CH_3CN$ in 50 mM aqueous solution of $Na_xPO_4$ (pH 5.8) (2%→50% $CH_3CN$ in 30 min) (4.6 mm ID×150 mm L; (5 μm pores)) in conjugation with a linear gradient of buffer B in buffer A (0→100% B in 30 min). Buffer B was 50% $CH_3CN$ in aqueous 50 mM sodium phosphate (pH 5.8). Buffer A was 2% $CH_3CN$ in aqueous 50 mM sodium phosphate (pH 5.8)). Fractions containing pure oligonucleotide, either with or without thiol-modifier synthon, were pooled, then desalted separately on a pre-equilibrated Sep-Pak™. Alternately, 0.1 M triethylammonium acetate (mobile phase A) and acetonitrile (mobile phase B) gradient (20% B to 100% B in 25 min (flow 1 mL/min, monitored 260 nm, Phenomenex Luna 5 μm, 4.6 mm×150 mm) was used. The S-CBz-protected containing oligomer was finally purified using a semi-preparative reversed-phase C18 column. The final yield was calculated from the absorbance at 260 nm using an UV spectrophotometer. The oligonucleotide is dried and stored until S-CBz deprotection.

Final deprotection of the 5'-CBz group to provide the thiol involves the treatment of the modified oligonucleotide with 0.1 M NaOH in methanol for 2.5 hours (Table 3). After which the NaOH is neutralized with $Na_xPO_4$ (pH 5.8) to a pH between 7 and 8. The Michael acceptor is then added and the conjugation reaction ensued.

All references cited herein are herein incorporated by reference in entirety.

It will be evident that various changes and modifications can be made to the teachings herein without departing from the spirit and scope of the invention.

I claim:
1. A compound of the formula:

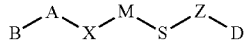

wherein B is phenyl; A is methylene; X is O or S; M is carbonyl (C=O); S is sulfur; Z is an aliphatic hydrocarbon of 1 to 6 carbons, and D is phosphoramidite.

2. The compound of claim 1, wherein X is O.
3. The compound of claim 1, wherein Z is hexyl.
4. A composition comprising a nucleic acid comprising phosphoramidite or phosphodiester monomers and the compound of claim 1 at the 5' terminus thereof.

* * * * *